United States Patent
Buyens

(10) Patent No.: US 9,042,583 B2
(45) Date of Patent: May 26, 2015

(54) MUSIC PRE-PROCESSING FOR HEARING PROSTHESES

(75) Inventor: Wim Buyens, New South Wales (AU)

(73) Assignee: Cochlear Limited, Macquarie University, NSW (AU)

( * ) Notice: Subject to any disclaimer, the term of this patent is extended or adjusted under 35 U.S.C. 154(b) by 971 days.

(21) Appl. No.: 13/163,343

(22) Filed: Jun. 17, 2011

(65) Prior Publication Data

US 2011/0280427 A1    Nov. 17, 2011

Related U.S. Application Data

(63) Continuation-in-part of application No. PCT/AU2009/001649, filed on Dec. 18, 2009.

(30) Foreign Application Priority Data

Dec. 19, 2008  (AU) ................................ 2008906548

(51) Int. Cl.
*H04R 25/00* (2006.01)
*A61N 1/36* (2006.01)

(52) U.S. Cl.
CPC ............ *H04R 25/50* (2013.01); *A61N 1/36032* (2013.01)

(58) Field of Classification Search
CPC ........... A61N 1/36032; H04R 2225/61; H04R 25/00; H04R 25/305; H04R 25/50; H04R 25/505; H04R 25/554

USPC ........ 381/312, 316, 320, 321; 600/28; 607/57
See application file for complete search history.

(56) References Cited

U.S. PATENT DOCUMENTS

2008/0031479 A1    2/2008  Sorgel

FOREIGN PATENT DOCUMENTS

| JP | 2000-102097 | 4/2000 |
|---|---|---|
| TW | 200818961 | 4/2008 |
| WO | 2008028484 | 3/2008 |
| WO | 2008092183 | 8/2008 |
| WO | 2009152442 | 12/2009 |

OTHER PUBLICATIONS

International Search Report and Written Opinion dated Feb. 9, 2010 for International Application No. PCT/AU2009/001649.

*Primary Examiner* — Davetta W Goins
*Assistant Examiner* — Phylesha Dabney
(74) *Attorney, Agent, or Firm* — McDonnell Boehnen Hulbert & Berghoff LLP

(57) ABSTRACT

A method of pre-processing a sound signal including music for an auditory prosthesis is provided. An input sound signal is received. The sound signal is processed using music pre-processing software to produce a music pre-processed signal. The music pre-processed signal is presented for further processing, so as to produce a corresponding stimuli signal.

19 Claims, 2 Drawing Sheets

MUSIC PRE-PROCESSING FOR HEARING PROSTHESES

PRIORITY APPLICATION

The present application is a continuation-in-part of and hereby incorporates by reference and claims priority under 35 U.S.C. §120 to International Application No. PCT/AU2009/001649 filed on Dec. 18, 2009, which claims priority to Australian Application No. 2008906548, filed on Dec. 19, 2008.

TECHNICAL FIELD

The present invention relates to processing music for auditory prostheses, particularly for cochlear implants and other neural stimulators.

BACKGROUND TO THE INVENTION

Auditory prostheses have been very successful in providing a percept of hearing, and accompanying speech perception, for sufferers of hearing impairment. Such prostheses include cochlear implants, brain stem implants, hearing aids, middle ear implants, and devices that combine electric and acoustic or mechanical stimulation, Sound processing strategies for auditory prostheses have tended to focus on speech, as it is the most important aspect for the user. However, it is also important to provide satisfactory performance for other sounds, particularly music. Applying conventional speech processing strategies to a musical performance does not generally produce a satisfactory result. For speech, relatively little information is required to enable at least a degree of understanding. In contrast, music typically has many simultaneous elements, all of which interact to produce a harmonious whole. This complexity cannot be reproduced by conventional speech processing strategies, and the result of applying such an approach to music does not create a satisfactory percept for most users. Some cochlear implant users have reported reasonably satisfactory outcomes where relatively simple music is concerned.

It is an object of the present invention to provide a sound processing strategy which provides improved performance for music for users of auditory prostheses.

SUMMARY OF THE INVENTION

In a broad form, the present invention applies, in the auditory prosthesis itself, a melody tracker approach to pre-process music, in real time, taking a complex musical input and outputting a simplified melody, such as a representation of a single voice derived from the complex musical input. This melody can then provide the input to the subsequent stages of sound processing and mapping. According to one aspect, the present invention provides a method of processing a sound signal for an auditory prosthesis, the method including at least the steps of:

receiving an input sound signal;

processing said input sound signal using music pre-processing software to produce a music pre-processed signal; and further processing said music pre-processed signal, so as to produce a corresponding stimuli signal.

The further processing may be conventional for the device in question.

According to another aspect, the present invention provides an auditory prosthesis, operatively adapted to process sound signals according to the above method.

By music pre-processing software, the present specification and claims mean software in the auditory prosthesis that can process an audio signal including a complex piece of music, and produce a signal in which the musical information is simplified or otherwise modified to emphasize musical aspects, and which is suitable for subsequent processing by the auditory prosthesis. Such processing is carried out in or near real time. One example of such software is a melody tracker. This is software that can process a complex piece of music, such as by buffering and/or examining one or more preceding samples from the complex piece of music, and determine a simple, tonal melody line, either as a data representation, or as an audio signal indicative of the melody in question. The melody line may be, for example, a human voice or instrumental, and the melody tracker preferably retains the timbre of the melody as well as the notes per se. Other examples of music pre-processing software include software that is capable of additionally or alternatively producing more complex derivatives of the music, for example beat trackers, chord pickers, and other such musical information extraction or sound source separation software.

This approach isolates the most important parts of the music, so as to improve the prospects that the music can be understood and perceived by the auditory prosthesis user.

BRIEF DESCRIPTION OF THE DRAWINGS

Illustrative embodiments of the present invention will now be described with reference to the accompanying figures, in which.

DETAILED DESCRIPTION

Figure 1:
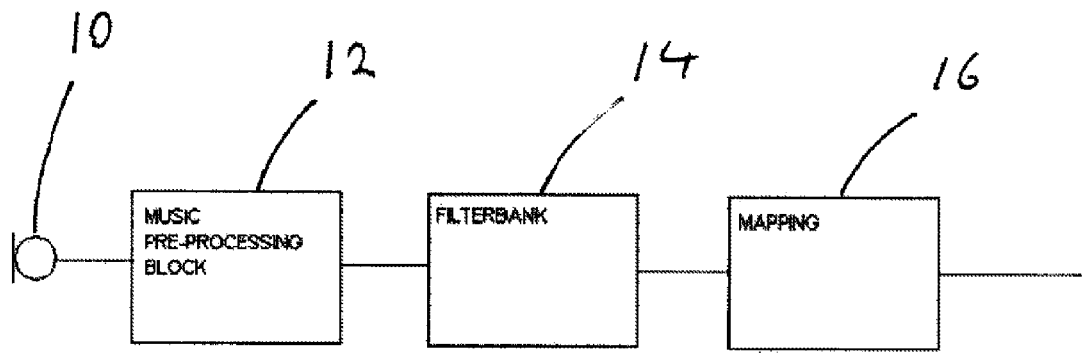
FIG. 1 is a block diagram illustrating the use of a music pre-processing block.

The present invention will be described with reference to a particular illustrative example, which is a device intended for use in a cochlear implant system. However, it will be appreciated that the present invention is not limited in context to such a system. It may be applied to a cochlear implant system such as a hybrid electrical/acoustic system, a hearing aid system, a middle ear implant, or any other suitable auditory prosthesis. It may be applied to a system with implanted components, or a fully external system. It will be appreciated that the present implementation is described for illustrative purposes, and its features are not intended to be limitative of the scope of the present invention. Many variations and additions are possible within the scope of the present invention. Benefits attributable to the described technology are most likely to be realized in users having severe to profound hearing loss, where residually sensed audio (sensed without assistance of the auditory prosthesis) does not interfere with the signal having simplified musical information.

The general principle of the present invention is to use a music preprocessing block, for example incorporating a melody tracker, prior to the normal Cochlear Implant (CI) signal processing path, in order to allow a simplified music signal (rather than a complex polyphonic signal) to be processed by the normal CI signal processing path. The effect of this is to improve the ratio of usable music signal to other sounds, in order to improve the prospect of an acceptable experience for the user. In this way, users with auditory prostheses may begin to enjoy music again or for the first time.

Melody tracker software has been developed for other purposes. For example such software has been used to extract a signal so that lyrics can be recognized, automatic music classification can be performed, melodies can be recognized. The principles and approaches of such systems are known in the field of music information retrieval, in which numerous techniques for real-time music source separation have been developed and are continued to be developed. Most of these techniques buffer a quantity of past samples to predict likely components of current and/or future samples. Certain characteristics, such as harmonics typically associated with singing voices or fast attack/decay typically associated with some percussion components, may be used to track a melody (or voice) as a song proceeds. The voice of interest can then be amplified (or other voices filtered out, such as by use of algorithms incorporating Fast Fourier Transforms (FFTs), etc.).

One reference, the contents of which are hereby incorporated by reference, that discusses many of these concepts (albeit by processing an entire song to provide a learning source model to separate voice, pitch, and singing voice) is "Separation of Singing Voice from Music Accompaniment for Monaural Recordings," IEEE Transactions on Audio, Speech, and Language Processing, Vol. 15, No. 4, May 2007, Yipeng Li, DeLiang Wang. According to one embodiment, the present implementation would apply variations of techniques similar to those described by Li and Wang to a buffered quantity of musical information (preferably not an entire song, as described in the Li and Wang paper) in order to provide a simplified music signal. Any other suitable melody tracker approach could be used.

In general, the effectiveness (accuracy) of real-time music source separation techniques depends on the quantity of information available (i.e. the amount of buffered music information, which is constrained by available memory resources, among other things) and the available processing power (i.e. speed). For a real-time application, such as perceiving a live musical performance, a delay of around 20 milliseconds or less between when a sound is "seen" (e.g. a singer's lips voice a particular sound) and "heard" (e.g. auditory stimulation provided), when the auditory device user is co-located with the musical performer(s). Delays longer than around 20 milliseconds will be less noticeable when the user is located a large distance from the performer(s); since sound travels much more slowly than light, the synchronization between sound and light would be off anyway, even for a user having unassisted hearing. In general, latency constraints for music can be somewhat relaxed compared to those for speech, in which lip-reading is important.

In one embodiment, the user is able to select between (1) a first device option that utilizes a relatively larger amount of buffered information to provide a more accurate representation of the source that is the target of the separated voice signal, but at a relatively longer delay, and (2) a second device option that utilizes relatively smaller amount of buffered information to provide a relatively less accurate representation (i.e. a noisier representation) of the source, but at a relatively shorter delay.

The basic signal path for a cochlear implant starts with a microphone 10 detecting a sound signal. The transduced signal is then pre-processed 12, and presented to a filterbank 14, which produces a series of outputs representative of amplitude in the channels defined by the filterbank. These outputs are then processed and mapped 16 to specific electrode locations and stimulation levels responsive to the filter output values and other factors, depending upon the stimulation strategy in use.

Referring to FIG. 1, according to this implementation of the present invention, the music pre-processing block 12 is placed as a pre-processing step, before the filterbank 14. It is preferred that a suitable switching arrangement be made available to the user, so that the user can determine whether or not to operate in the music mode.

The melody tracker functions to process the audio signal using melody tracker software, such as a real-time software routine known by those in the field of real-time music source separation, in order to detect and separate out a signal corresponding to the melody. In a conventional track, such as a pop music track, the tracker would identify the lead singer's voice. In an instrumental track, it would identify the instrument which is carrying the main melody, or in a more complex piece, it may track the melody through various instruments as the melody moves through the band. This detected melody component is separated out and presented as an input to the filterbank and subsequent stages of processing. In principle, the part of the signal that has the most value in understanding the music is emphasized relative to the rest of the signal for a user of an auditory device.

Figure 2:
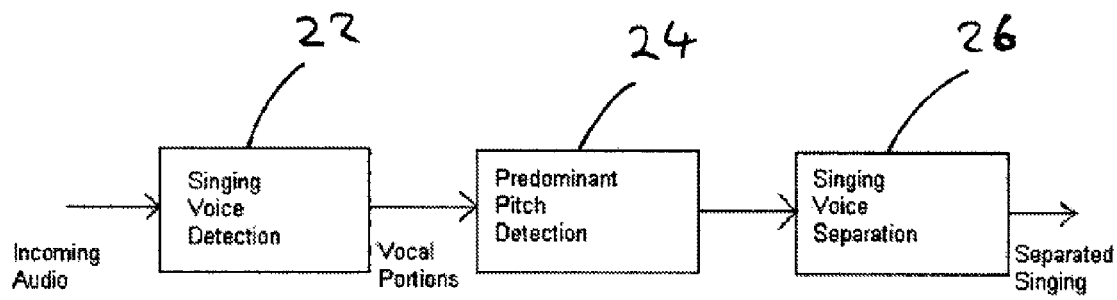
FIG. 2 is a block diagram illustrating the operation of an illustrative melody tracker.

FIG. 2 illustrates one possible melody tracker process, particularly described in the paper by Li and Wang mentioned above. In this process, the incoming audio signal (as appropriately buffered to realize a desired accuracy/delay balance) is first processed to detect voice elements 22. Within each voice portion, the predominant pitch is detected 24. This pitch information is then used to identify the singing voice components, which are in turn separated 26, so as to provide a separated singing voice track. It is such a signal that is in turn used as the basis for processing. It is preferred that the melody tracker preserves the timbre of the melody, rather than simply produce (for example) audio tones.

Other types of music processing software may be used, for example multi-pitch detection algorithms, melody trackers, beat trackers, chord pickers and other music information retrieval or sound source separation algorithms. The simple melody tracker described above may simplify the music too much for some users and some musical pieces. These other types of algorithms may provide some additional data, but with a simpler set of data for processing than the full musical score would otherwise provide.

Figure 3:
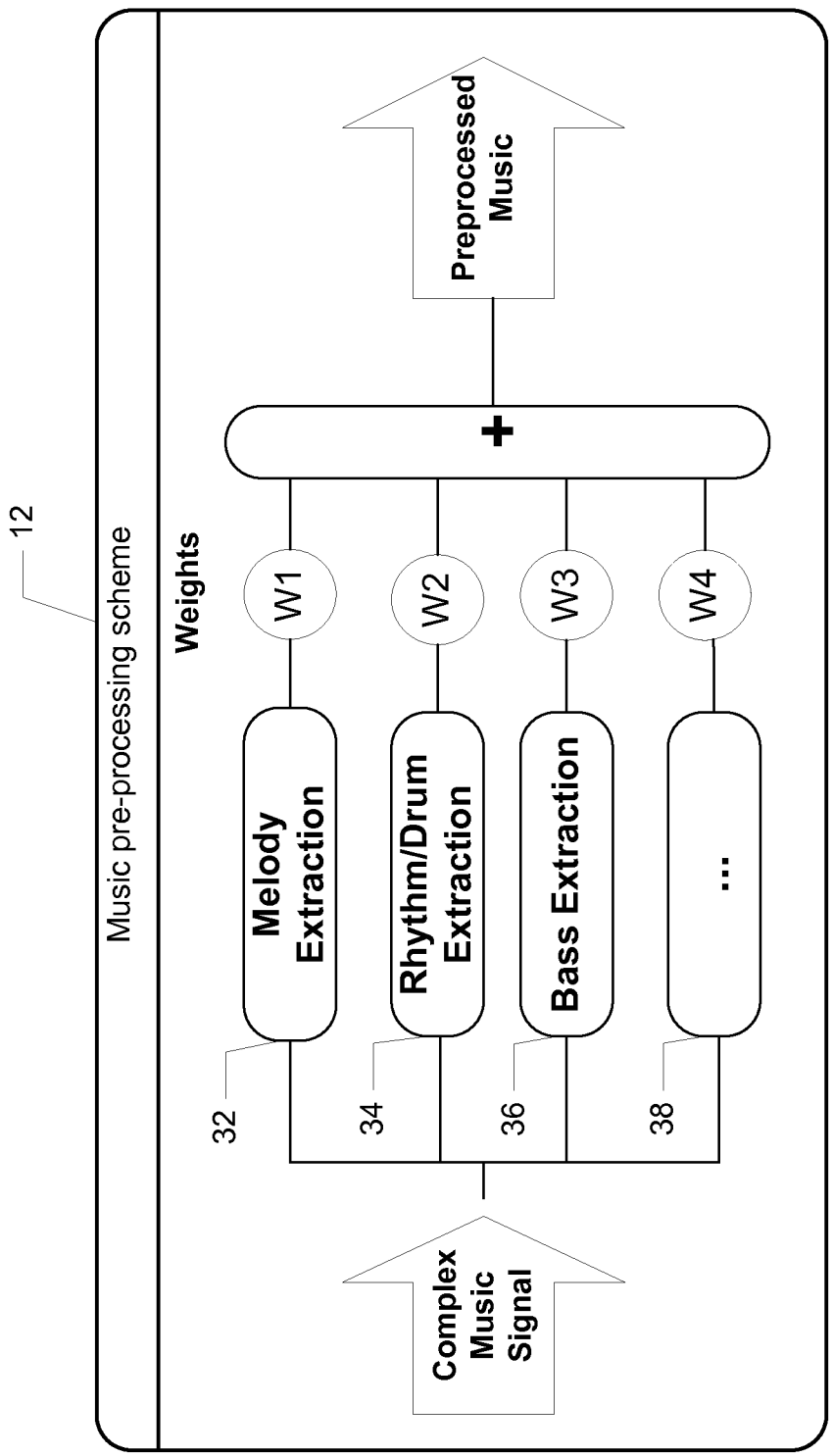
FIG. 3 is a block diagram illustrating the combination of different sound source separation algorithms that are combined using weighting factors in order to amplify preferred instruments or components and attenuate undesirable instruments or components.

FIG. 3 illustrates an example of a pre-processing block 12 which utilizes a number of different music processing software acting in parallel. Each type extracts different elements of the audio signal. In addition to the melody tracker 32, there is expressly shown a rhythm/drum tracker 34, a bass tracker 36 and options for other forms of music information retrieval or sound source separation 38. Each tracker operates in parallel to extract different relevant characteristics of the audio signal. As shown, the output from each tracker is weighted 40, ideally under the control of the user, to provide a balance of the different extracted music characteristics in accordance with the user's preferences. The weighted signals are combined to provide the pre-processed signal which is forwarded to the filterbank 14.

Imagine for example an instrumental piece of music without a clear melody. In this case a chord picker can be a good tool to simplify the music, in the case that these chords represent the music reasonably well. In a suitable implementation, a variety of such tools could be made available to the users to allow them to make their own selection of what is appropriate in the circumstances, which could include the genre of music, and their own particular hearing capacity. The system could alternatively automatically select one or more music pre-processing tools, responsive for example to the musical genre. A general requirement is that the processing can be done online in real-time, so that a recipient can, for example, go to a live concert and not have to listen to a modified pre-recorded sound file. In addition, all such pre-processing, selecting, and weighting is performed in the auditory prosthesis, rather than in a remote processing device. The weighting 40 described above and as set forth in FIG. 3 utilizes concepts that are somewhat similar to so-called beamforming techniques presently used by some auditory prosthesis devices to distinguish target speech coming from the front from noise coming from a different direction. In beamforming, two microphones are used, each positioned so that speech (or other sound) originating from in front of a person is received at a maximal delay between the two microphones, while noise originating from 90-degrees relative to the front of the person is received by both microphones simultaneously (i.e. no delay). To improve signal-to-noise ratio under this beamforming system, the auditory prosthesis device attenuates the noise (received with no delay) as much as possible and may amplify the speech (received with maximum delay). In a similar manner, according to presently described technology, melody-to-background ratio (i.e. analogous to signal-to-noise ratio) may be improved or adjusted as desired by attenuating or applying lesser weight to certain sound sources (e.g. percussion and other background music), while amplifying or applying greater weight to other sound sources, such as a vocal melody, for example.

The invention claimed is:

1. A method for pre-processing a musical sound signal in an auditory prosthesis, comprising:
   receiving at a microphone associated with the auditory prosthesis a sound signal comprising musical information;
   storing in a memory of the auditory prosthesis a buffer comprising a quantity of the musical information from the sound signal;
   pre-processing the sound signal using the quantity of the buffered musical information stored in the memory to produce a music pre-processed signal;
   providing the music pre-processed signal for further processing in the auditory prosthesis, the further processing being used to produce a corresponding stimuli signal; and
   providing a selection of music pre-processing software options to use for pre-processing the sound signal.

2. The method of claim 1, wherein pre-processing the sound signal comprises applying a melody tracker software routine to the sound signal.

3. The method of claim 2, wherein the melody tracker software routine preserves at least part of the timbre of a melody component of the musical information.

4. The method of claim 2, wherein the selection of music pre-processing software options comprises a selection of whether to apply the melody tracker software routine or an alternative pre-processing software routine.

5. The method of claim 1, wherein pre-processing the sound signal includes:
   applying a plurality of different trackers to respectively extract different components of the sound signal, wherein the selection of music pre-processing software options comprises an option to select different weightings to be applied to the output of each tracker, the weighted outputs being combined to produce the music pre-processed signal.

6. The method of claim 1, wherein the selection of music pre-processing software options comprises an option to select between at least a first option in which the music pre-processed signal has a relatively better accuracy but a relatively longer delay and a second option in which the music pre-processed signal has a relatively worse accuracy but a relatively shorter delay.

7. A method for pre-processing a musical sound signal in an auditory prosthesis, comprising:
   receiving at a microphone associated with the auditory prosthesis a sound signal comprising musical information;
   storing in a memory of the auditory prosthesis a buffer comprising a quantity of the musical information from the sound signal;
   pre-processing the sound signal using the quantity of the buffered musical information stored in the memory to produce a music pre-processed signal;
   providing the music pre-processed signal for further processing in the auditory prosthesis, the further processing being used to produce a corresponding stimuli signal; and
   selecting at least one music pre-processing software option based on content of the sound signal.

8. A method for providing a simplified musical signal with an implantable auditory prosthesis, comprising:
   receiving at a microphone associated with the auditory prosthesis a sound signal comprising musical information;
   storing in a memory of the auditory prosthesis a buffer comprising a quantity of the musical information from the sound signal;
   pre-processing the sound signal using the quantity of the buffered musical information stored in the memory to produce a music pre-processed signal;
   providing the music pre-processed signal to a filterbank to produce a series of outputs representative of amplitude in the channels defined by the filterbank; and
   using the series of outputs to apply stimulation to at least one site associated with the auditory prosthesis,
   wherein using the series of outputs to apply stimulation to at least one site associated with the auditory prosthesis comprises mapping the series of outputs to a plurality of specific electrode locations and stimulation levels.

9. The method of claim 8, wherein the implantable auditory prosthesis is a cochlear implant prosthesis, wherein the microphone is located on a behind-the-ear (BTE) component of the cochlear implant prosthesis, and wherein the specific electrode locations are locations on at least one cochlear stimulation electrode.

10. The method of claim 8, further comprising presenting an option to select between at least a first option in which the music pre-processed signal has a relatively better accuracy but a relatively longer delay and a second option in which the music pre-processed signal has a relatively worse accuracy but a relatively shorter delay.

11. The method of claim 8, wherein pre-processing the sound signal comprises applying a melody tracker software routine to the sound signal.

12. The method of claim 11, wherein the melody tracker software routine preserves at least part of the timbre of a melody component of the musical information.

13. The method of claim 11, further comprising providing a selection of whether to apply the melody tracker software routine or an alternative pre-processing software routine.

14. The method of claim 8, further comprising providing a selection of music pre-processing software options to use for pre-processing the sound signal.

15. The method of claim 8, wherein pre-processing the sound signal includes:
applying a plurality of different trackers to respectively extract different components of the sound signal; and
presenting an option to select different weightings to be applied the output of each tracker, the weighted outputs being combined to produce the music pre-processed signal.

16. The method of claim 8, further comprising selecting at least one music pre-processing software option based on content of the sound signal.

17. An auditory prosthesis, comprising:
a microphone receiving a sound signal comprising musical information;
a memory for storing a buffer comprising a quantity of the musical information from the sound signal;
a pre-processing block for pre-processing the sound signal using the quantity of the buffered musical information stored in the memory to produce a music pre-processed signal;
a filterbank to produce from the music pre-processed signal a series of outputs representative of amplitude in the channels defined by the filterbank; and
at least one stimulation site to which the series of outputs are provided at a respective determined stimulation level,
wherein at least the microphone and the memory are located on a behind-the-ear component of the auditory prosthesis,
and wherein the at least one stimulation site is located on a portion of a cochlear stimulation electrode.

18. A method for pre-processing a musical sound signal in an auditory prosthesis, comprising:
receiving at a microphone associated with the auditory prosthesis a sound signal comprising musical information;
storing in a memory of the auditory prosthesis a buffer comprising a quantity of the musical information from the sound signal;
pre-processing the sound signal using the quantity of the buffered musical information stored in the memory to produce a music pre-processed signal, wherein pre-processing the sound signal includes:
applying a plurality of different trackers to respectively extract different components of the sound signal; and
presenting an option to select different weightings to be applied to the output of each tracker, the weighted outputs being combined to produce the music pre-processed signal; and
providing the music pre-processed signal for further processing in the auditory prosthesis, the further processing being used to produce a corresponding stimuli signal.

19. A method for providing a simplified musical signal with an implantable auditory prosthesis, comprising:
receiving at a microphone associated with the auditory prosthesis a sound signal comprising musical information;
storing in a memory of the auditory prosthesis a buffer comprising a quantity of the musical information from the sound signal;
pre-processing the sound signal using the quantity of the buffered musical information stored in the memory to produce a music pre-processed signal;
presenting an option to select between at least a first option in which the music pre-processed signal has a relatively better accuracy but a relatively longer delay and a second option in which the music pre-processed signal has a relatively worse accuracy but a relatively shorter delay;
providing the music pre-processed signal to a filterbank to produce a series of outputs representative of amplitude in the channels defined by the filterbank; and
using the series of outputs to apply stimulation to at least one site associated with the auditory prosthesis.

* * * * *